US009950173B2

(12) United States Patent
Doan

(10) Patent No.: US 9,950,173 B2
(45) Date of Patent: Apr. 24, 2018

(54) SYSTEM AND METHOD FOR DELIVERING SUB-THRESHOLD AND SUPER-THRESHOLD THERAPY TO A PATIENT

(71) Applicant: Boston Scientific Neuromodulation Corporation, Valencia, CA (US)

(72) Inventor: Que T. Doan, West Hills, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 745 days.

(21) Appl. No.: 14/295,735

(22) Filed: Jun. 4, 2014

(65) Prior Publication Data
US 2014/0364919 A1 Dec. 11, 2014

Related U.S. Application Data
(60) Provisional application No. 61/832,083, filed on Jun. 6, 2013.

(51) Int. Cl.
*A61N 1/32* (2006.01)
*A61N 1/36* (2006.01)
*A61N 1/372* (2006.01)

(52) U.S. Cl.
CPC ..... *A61N 1/36164* (2013.01); *A61N 1/36071* (2013.01); *A61N 1/36132* (2013.01);
(Continued)

(58) Field of Classification Search
CPC ............ A61N 1/36071; A61N 1/36185; A61N 1/37247; A61N 1/36139; A61N 1/36164;
(Continued)

(56) References Cited

U.S. PATENT DOCUMENTS 6,516,227 B1   2/2003   Meadows et al.
6,675,046 B2   1/2004   Holsheimer
(Continued)

FOREIGN PATENT DOCUMENTS

WO   WO-2006029257 A2   3/2006
WO   WO-2006135791 A2   12/2006
(Continued)

OTHER PUBLICATIONS

Rao, Prakash, et al., "Technique for Linking Electrodes Together During Programming of Neurostimulation System", U.S. Appl. No. 61/561,760, filed Nov. 18, 2011.
(Continued)

*Primary Examiner* — Michael Carey
(74) *Attorney, Agent, or Firm* — Schwegman Lundberg & Woessner, P.A.

(57) ABSTRACT

A neuromodulation system includes modulation output circuitry and control circuitry. The modulation output circuitry may be configured to deliver therapeutic electrical energy including therapeutic sub-threshold electrical energy and therapeutic a super-threshold electrical energy. The sub-threshold electrical energy is below a patient-perception threshold and the super-threshold electrical energy is above the patient-perception threshold. The patient-perception threshold is a boundary below which a patient does not sense delivery of the electrical energy and above which the patient does sense delivery of the electrical energy. The control circuitry is configured to control the modulation output circuitry to deliver the therapeutic electrical energy using alternating cycles of the sub-threshold electrical energy below the patient-perception threshold and the super-threshold electrical energy above the patient-perception-threshold.

20 Claims, 7 Drawing Sheets

(52) U.S. Cl.
CPC ..... *A61N 1/36139* (2013.01); *A61N 1/36178* (2013.01); *A61N 1/36185* (2013.01); *A61N 1/37247* (2013.01)

(58) Field of Classification Search
CPC ............ A61N 1/36187; A61N 1/36132; A61N 1/36189; A61N 1/37241; A61N 1/0551; A61N 1/36178; A61N 1/36464
USPC .......................................................... 607/46
See application file for complete search history.

(56) References Cited

U.S. PATENT DOCUMENTS

| | | | |
|---|---|---|---|
| 6,895,280 | B2 | 5/2005 | Meadows et al. |
| 6,993,384 | B2 | 1/2006 | Bradley et al. |
| 7,317,948 | B1 | 1/2008 | King et al. |
| 7,333,857 | B2 | 2/2008 | Campbell |
| 7,539,538 | B2 | 5/2009 | Parramon et al. |
| 7,650,184 | B2 | 1/2010 | Walter |
| 7,979,133 | B2 | 7/2011 | Feler et al. |
| 8,019,439 | B2 | 9/2011 | Kuzma et al. |
| 8,224,453 | B2 | 7/2012 | De Ridder |
| 8,255,057 | B2 | 8/2012 | Fang et al. |
| 8,355,797 | B2 | 1/2013 | Caparso et al. |
| 8,380,318 | B2 | 2/2013 | Kishawi et al. |
| 8,455,716 | B2 | 6/2013 | Huang et al. |
| 8,504,147 | B2 | 8/2013 | Deem et al. |
| 8,615,300 | B2 | 12/2013 | Feler et al. |
| 8,649,874 | B2 | 2/2014 | Alataris et al. |
| 8,670,831 | B2 | 3/2014 | Wacnik et al. |
| 8,676,329 | B2 | 3/2014 | Wacnik et al. |
| 8,676,331 | B2 | 3/2014 | Parker |
| 8,731,675 | B2 | 5/2014 | Ranu et al. |
| 8,751,009 | B2 | 6/2014 | Wacnik |
| 2003/0139781 | A1 | 7/2003 | Bradley et al. |
| 2004/0215286 | A1* | 10/2004 | Stypulkowski .... A61N 1/37211 607/48 |
| 2007/0150036 | A1 | 6/2007 | Anderson |
| 2008/0188909 | A1 | 8/2008 | Bradley |
| 2009/0204173 | A1 | 8/2009 | Fang et al. |
| 2010/0010566 | A1 | 1/2010 | Thacker et al. |
| 2010/0023070 | A1* | 1/2010 | Moffitt ............... A61N 1/36071 607/2 |
| 2010/0121409 | A1 | 5/2010 | Kothandaraman et al. |
| 2010/0191307 | A1 | 7/2010 | Fang et al. |
| 2010/0249875 | A1 | 9/2010 | Kishawi et al. |
| 2010/0274312 | A1* | 10/2010 | Alataris ............. A61N 1/36071 607/46 |
| 2010/0274314 | A1 | 10/2010 | Alataris et al. |
| 2010/0274315 | A1 | 10/2010 | Alataris et al. |
| 2010/0274317 | A1 | 10/2010 | Parker et al. |
| 2010/0274318 | A1 | 10/2010 | Walker et al. |
| 2010/0274326 | A1 | 10/2010 | Chitre et al. |
| 2012/0059446 | A1 | 3/2012 | Wallace et al. |
| 2012/0083709 | A1 | 4/2012 | Parker et al. |
| 2012/0253422 | A1 | 10/2012 | Thacker et al. |
| 2012/0265279 | A1 | 10/2012 | Zhu |
| 2012/0283797 | A1 | 11/2012 | De Ridder |
| 2012/0290041 | A1 | 11/2012 | Kim et al. |
| 2013/0066411 | A1 | 3/2013 | Thacker et al. |
| 2013/0116752 | A1 | 5/2013 | Parker et al. |
| 2013/0268021 | A1 | 10/2013 | Moffitt |
| 2013/0296975 | A1 | 11/2013 | Lee et al. |
| 2014/0081349 | A1 | 3/2014 | Lee et al. |

FOREIGN PATENT DOCUMENTS

| | | |
|---|---|---|
| WO | WO-2009061813 A1 | 5/2009 |
| WO | WO-2014197564 A1 | 12/2014 |

OTHER PUBLICATIONS

Vansickle, Dennis Allen, et al., "Neuromodulation System and Method for Transitioning Between Programming Modes", U.S. Appl. No. 14/214,752, filed Mar. 15, 2014.

Vansickle, Dennis Allen, "Systems and Methods for Delivering Sub-threshold Therapy to a Patient", U.S. Appl. No. 61/801,917, filed Mar. 15, 2013.

"International Application Serial No. PCT/US2014/40860, International Preliminary Report on Patentability dated Dec. 17, 2015", 8 pgs.

"International Application Serial No. PCT/US2014/40860, International Search Report dated Oct. 9, 2014", 3 pgs.

"International Application Serial No. PCT/US2014/40860, Written Opinion dated Oct. 9, 2014", 6 pgs.

* cited by examiner

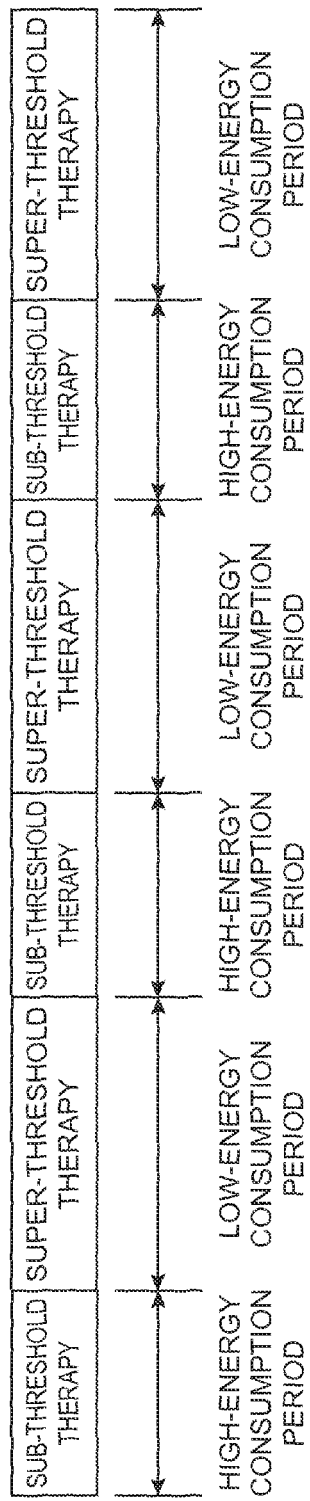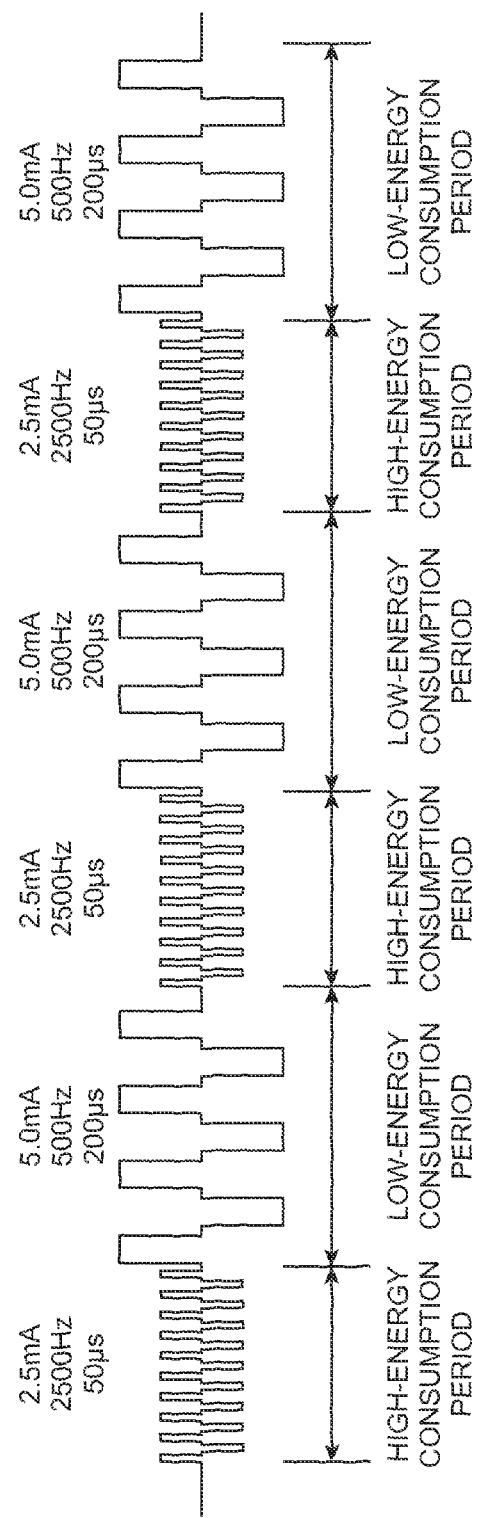
FIG. 6
FIG. 7

SYSTEM AND METHOD FOR DELIVERING SUB-THRESHOLD AND SUPER-THRESHOLD THERAPY TO A PATIENT

CLAIM OF PRIORITY

This application claims the benefit of priority under 35. U.S.C. § 119(e) of U.S. Provisional Parent Application Ser. No. 61/832,083, filed on Jun. 6, 2013, which is herein incorporated by reference in its entirety.

FIELD OF THE INVENTION

The present inventions relate to tissue modulation systems, and more particularly, to programmable able neuromodulation systems.

BACKGROUND OF THE INVENTION

Implantable neuromodulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, in recent investigations, Peripheral Nerve Stimulation (PNS) systems have demonstrated efficacy in the treatment of chronic pain syndromes and incontinence, and a number of additional applications are currently under investigation. Furthermore, Functional Electrical Stimulation (FES) systems, such as the Freehand system by NeuroControl (Cleveland, Ohio), have been applied to restore some functionality to paralyzed extremities in spinal cord injury patients.

These implantable neuromodulation systems typically include one or more electrode carrying stimulation leads, which are implanted at the desired stimulation site, and an implantable neuromodulation device (e.g., an implantable pulse generator (IPG)) implanted remotely from the stimulation site, but coupled either directly to the neuromodulation leads) or indirectly to the neuromodulation lead(s) via a lead extension. The neuromodulation system may further comprise a handheld external control device (e.g., a remote control (RC)) to remotely instruct the neuromodulator to generate electrical stimulation pulses in accordance with selected stimulation parameters.

Implantable neuromodulation devices are active devices requiring energy for operation, and thus, the neuromodulation system oftentimes include an external charger to recharge a neuromodulation device, so that a surgical procedure to replace a power depleted neuromodulation device can be avoided. To wirelessly convey energy between the external charger and the implanted neuromodulation device, the charger typically includes an alternating current (AC) charging coil that supplies energy to a similar charging coil located in or on the neuromodulation device. The energy received by the charging coil located on the neuromodulation device can then be stored in a rechargeable battery within the neuromodulation device, which can then be used to power the electronic componentry on-demand.

Electrical modulation energy may be delivered from the neuromodulation device to the electrodes in the form of an electrical pulsed waveform. Thus, electrical energy may be controllably delivered to the electrodes to therapeutically modulate neural tissue. The configuration of electrodes used to deliver electrical pulses to the targeted tissue constitutes an electrode configuration, with the electrodes capable of being selectively programmed to act as anodes (positive), cathodes (negative), or left off (zero). In other words, an electrode configuration represents the polarity being positive, negative, or zero. Other parameters that may be controlled or varied include the amplitude, width, and rate of the electrical pulses (which may be considered electrical pulse parameters) provided through the electrode array. Each electrode configuration, along with the electrical pulse parameters, can be referred to as a "modulation parameter set."

With some neuromodulation systems, and in particular, those with independently controlled current or voltage sources, the distribution of the current to the electrodes (including the case of the neuromodulation device, which may act as an electrode) may be varied such that the current is supplied via numerous different electrode configurations. In different configurations, the electrodes may provide current or voltage in different relative percentages of positive and negative current or voltage to create different electrical current distributions (i.e., fractionalized electrode configurations).

As briefly discussed above, an external control device can be used to instruct the neuromodulation device to generate electrical pulses in accordance with the selected modulation parameters. Typically, the modulation parameters programmed into the neuromodulation device can be adjusted by manipulating controls on the handheld external control device to modify the electrical modulation energy provided by the neuromodulation device system to the patient. Thus, in accordance with the modulation parameters programmed by the external control device, electrical pulses can be delivered from the neuromodulation device to the electrode(s) to modulate a volume of tissue in accordance with a set of modulation parameters and provide the desired efficacious therapy to the patient. The best modulation set will typically be one that delivers modulation energy to the volume of tissue that must be modulated in order to provide the therapeutic benefit (e.g., treatment of pain), while minimizing the volume of non-target tissue that is modulated.

However, the number of electrodes available, combined with the ability to generate a variety of complex electrical pulses, presents a huge selection of modulation parameter sets to the clinician or patient. For example, if the neuromodulation system to be programmed has an array of sixteen electrodes, millions of modulation parameter sets may be available for programming into the neuromodulation system. Today, neuromodulation systems may have up to thirty-two electrodes, thereby exponentially increasing the number of modulation parameters sets available for programming.

To facilitate such selection, the clinician generally programs the neuromodulation device through a computerized programming system. This programming system can be a self-contained hardware/software system, or can be defined predominantly by software running on a standard personal computer (PC). The PC or custom hardware may actively control the characteristics of the electrical stimulation generated by the neuromodulation device to allow the optimum stimulation parameters to be determined based on patient feedback or other means and to subsequently program the neuromodulation device with the optimum modulation parameter sets.

For example, in order to achieve an effective result from conventional SCS, the lead or leads must be placed in a location, such that the electrical modulation energy (in this case, electrical stimulation energy) creates a sensation known as paresthesia, which can be characterized as an alternative sensation that replaces the pain signals sensed by the patient. The paresthesia induced by the stimulation and perceived by the patient should be located in approximately the same place in the patient's body as the pain that is the target of treatment. If a lead is not correctly positioned, it is possible that the patient will receive little or no benefit from an implanted SCS system. Thus, correct lead placement can mean the difference between effective and ineffective pain therapy. When electrical leads are implanted within the patient, the computerized programming system, in the context of an operating room (OR) mapping procedure, may be used to instruct the neuromodulation device to apply electrical stimulation to test placement of the leads and/or electrodes, thereby assuring that the leads and/or electrodes are implanted in effective locations within the patient.

Once the leads are correctly positioned, a fitting procedure, which may be referred to as a navigation session, may be performed using the computerized programming system to program the external control device, and if applicable the neuromodulation device, with a set of modulation parameters that best addresses the painful site. Thus, the navigation session may be used to pinpoint volume of activation (VOA) or areas correlating to the pain. Such programming ability is particularly advantageous for targeting the tissue during implantation, or after implantation should the leads gradually or unexpectedly move that would otherwise relocate the stimulation energy away from the target site. By reprogramming the neuromodulation device (typically by independently varying the stimulation energy on the electrodes), the volume of activation (VOA) can often be moved back to the effective pain site without having to re-operate on the patient in order to reposition the lead and its electrode array. When adjusting the volume of activation (VOA) relative to the tissue, it is desirable to make small changes in the proportions of current, so that changes in the spatial recruitment of nerve fibers will be perceived by the patient as being smooth and continuous and to have incremental targeting capability.

Although alternative or artifactual sensations are usually tolerated relative to the sensation of pain, patients sometimes report these sensations to be uncomfortable, and therefore, they can be considered an adverse side-effect to neuromodulation therapy in some cases. Because the perception of paresthesia has been used as an indicator that the applied electrical energy is, in fact, alleviating the pain experienced by the patient, the amplitude of the applied electrical energy is generally adjusted to a level that causes the perception of paresthesia. It has been shown, however, that the delivery of sub-threshold electrical energy (e.g., high frequency pulsed electrical energy and/or low pulse width electrical energy) can be effective in providing neuromodulation therapy for chronic pain without causing paresthesia.

Although high-frequency modulation therapies have shown good efficacy in early studies, one notable drawback is the relatively high energy requirement to achieve high-frequency modulation in contrast to lower frequency stimulation techniques. In particular, the amount of energy required to generate an electrical waveform is proportional to the frequency of the electrical waveform. Thus, neuromodulation devices that generate relatively low frequency modulation energy typically need to be recharged only once every 1-2 weeks, whereas neuromodulation devices that generate relatively high frequency modulation energy may require a daily or more frequent recharge.

In order to conserve energy during high-frequency modulation therapy, it is suggested that the delivery of the high-frequency modulation energy to the patient be alternately bursted on and off, with the hope that the therapy provided when the high-frequency modulation energy is bursted on will have a lasting effect during the period during which the high-frequency modulation energy has been bursted off. However, continued therapy during the periods that the high-frequency modulation energy has been bursted off is not guaranteed.

There, thus, is a need to ensure that therapy is continued during a high-frequency modulation regimen while still minimizing energy consumption.

SUMMARY OF THE INVENTION

In accordance with one aspect of the present inventions, a neuromodulation system is provided. The neuromodulation system comprises a plurality of electrical terminals configured for being respectively coupled to a plurality of electrodes, and modulation output circuitry configured for delivering a sub-threshold electrical energy (e.g., a pulse train having a pulse rate greater than 1500 Hz and/or a pulse width less than 500 µs) to a first set of the electrical terminals, and for delivering a super-threshold electrical energy (e.g., a pulse train having a pulse rate less than 1500 Hz and/or a pulse width greater than 500 µs) to a second set of the electrical terminals. The sub-threshold level may be referred to as a patient-perception threshold, which may be referred to as a boundary below which a patient does not sense delivery of the electrical energy and above which the patient does sense delivery of the electrical energy. For example, in a spinal cord modulation system, the patient-perception threshold may be a boundary below which a patient does not experience paresthesia. The first and second electrical terminals may be the same as each other or different from each other.

The neuromodulation system further comprises control circuitry configured for controlling the modulation output circuitry in an automated manner that alternately cycles the sub-threshold electrical energy on during high-energy consumption therapy periods and off during low-energy consumption therapy periods, and that alternately cycles the sub-threshold electrical energy on during the low energy consumption therapy periods and off during the high energy consumption therapy periods. The high-energy consumption therapy periods may be interleaved with the low-energy consumption therapy periods, e.g., in a non-overlapping manner.

The neurostimulation system optionally comprises a user interface configured for receiving input from a user. In one case, the control circuitry may be configured for modifying at least one of the sub-threshold electrical energy and the super-threshold electrical energy in response to the input from the user. In another case, the control circuitry is configured for storing a time schedule in the memory in response to the input from the user, and defining the high-energy consumption therapy periods and low-energy consumption therapy periods in accordance with the time schedule. The neurostimulation system optionally comprises a sensor configured for detecting a patient activity level, in which case, the control circuitry is configured for defining the high-energy consumption therapy periods during times when the patient activity level is relatively high, and defining the low-energy consumption therapy periods during times when the patient activity level is relatively low.

The neuromodulation system may further comprise memory configured for storing a predetermined tissue modulation regimen, wherein the control circuitry is configured for controlling the modulation output circuitry to automatically cycle each of the sub-threshold electrical energy and the super-threshold electrical energy on and off in accordance with the predetermined tissue modulation regimen. The predetermined tissue modulation regimen may define a sub-threshold modulation program and a super-threshold modulation program, in which case, the modulation output circuitry may be configured for delivering the sub-threshold electrical energy to the first electrical terminal set in accordance with the sub-threshold modulation program, and delivering the super-threshold electrical energy to the first electrical terminal set in accordance with the super-threshold modulation program. The neuromodulation system may further comprise a casing containing the plurality of electrical terminals, the modulation output circuitry, and the control circuitry.

In accordance with another aspect of the present invention, a method of providing therapy to a patient is provided. The method comprises delivering a sub-threshold electrical energy (e.g., a pulse train having a pulse rate greater than 1500 Hz and/or a pulse width less than 500 μs) to a first tissue region (e.g., spinal cord tissue) of the patient, and delivering a super-threshold electrical energy (e.g., a pulse train having a pulse rate less than 1500 Hz and/or a pulse width greater than 500 μs) to a second tissue region (e.g., spinal cord tissue) of the patient. The first and second tissue regions may be the same as each other or different from each other. The sub-threshold electrical energy is alternately cycled on during high-energy consumption therapy periods and off during low-energy consumption therapy periods, thereby providing the therapy (e.g., alleviation of chronic pain) to the patient, and the super-threshold electrical energy is alternately cycled on during the low energy consumption therapy periods and off during the high energy consumption therapy periods, thereby supplementing the therapy provided to the patient. The high-energy consumption therapy periods may be interleaved with the low-energy consumption therapy periods, e.g., in a non-overlapping manner.

An optional method comprises receiving input from a user. In one case, at least one of the sub-threshold electrical energy and the super-threshold electrical energy is modified in response to the input from the user. In another case, a time schedule is stored in response to the input from the user, and the high-energy consumption therapy periods and low-energy consumption therapy periods are defined in accordance with the time schedule. Another optional method further comprises detecting a patient activity level, and defining the high-energy consumption therapy periods during times when the patient activity level is relatively high, and defining the low-energy consumption therapy periods during times when the patient activity level is relatively low. Still another method further comprises storing a predetermined tissue modulation regimen, wherein each of the sub-threshold electrical energy and the super-threshold electrical energy are cycled on and off in accordance with the predetermined tissue modulation regimen. The predetermined tissue modulation regimen may define a sub-threshold modulation program and a super-threshold modulation program, in which case, the sub-threshold electrical energy is delivered to the first tissue region in accordance with the sub-threshold modulation program, and the super-threshold electrical energy is delivered to the second tissue region in accordance with the super-threshold modulation program.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 6 is a timing diagram illustrating the sub-threshold therapy and super-threshold therapy being cycled on and off by the IPG of FIG. 3;

FIG. 7 is a timing diagram illustrating a sub-threshold electrical pulse train and a super-threshold electrical pulse train being cycled on and off by the IPG of FIG. 3;

DETAILED DESCRIPTION OF THE EMBODIMENTS

The description that follows relates to a spinal cord modulation (SCM) system. However, it is to be understood that the while the invention lends itself well to applications in SCM, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

Figure 1:
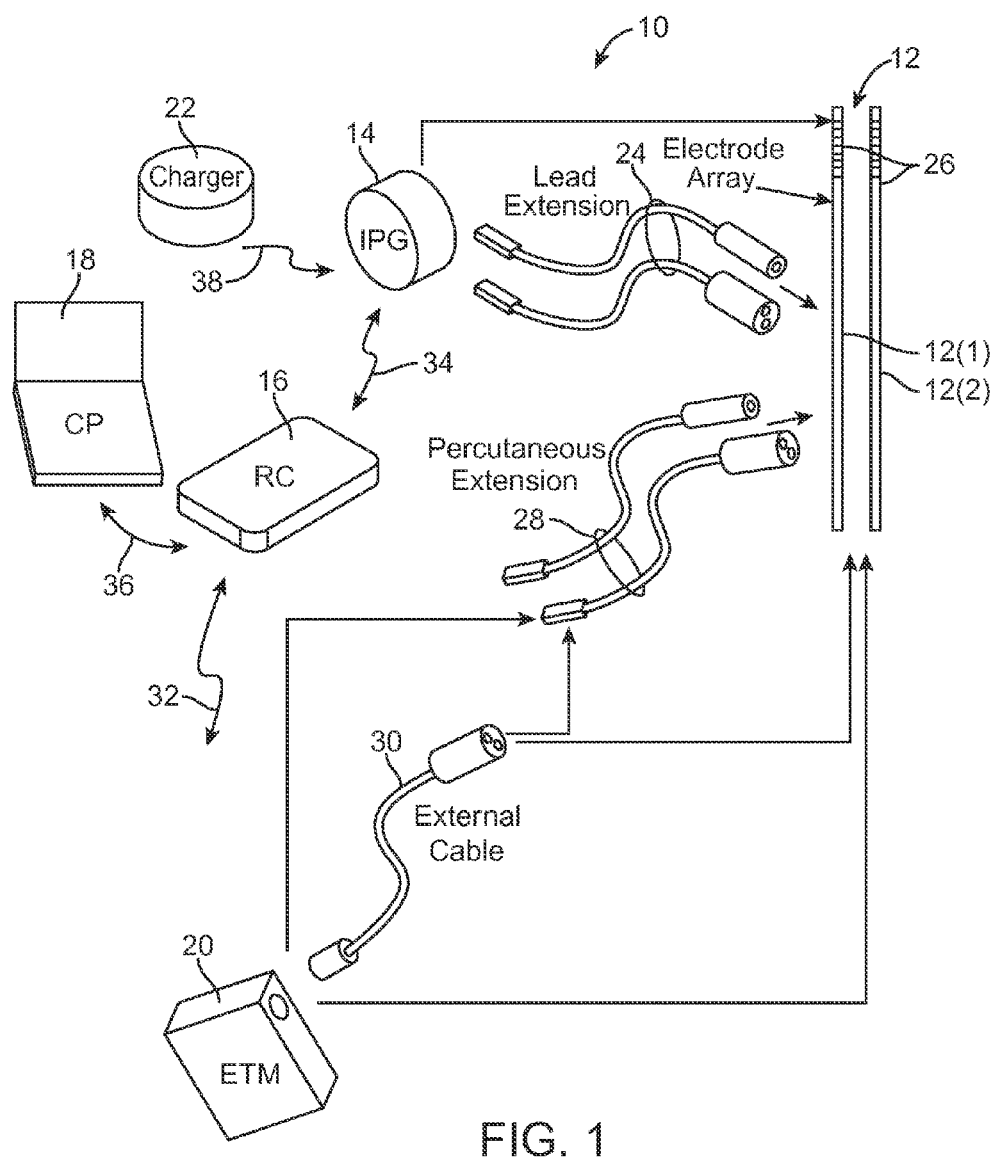
FIG. 1 is a plan view of a Spinal Cord Modulation (SCM) system constructed in accordance with one embodiment of the present inventions.

Turning first to FIG. 1, an exemplary SCM system 10 generally includes a plurality (in this case, two) of implantable neuromodulation leads 12, an implantable pulse generator (IPG) 14, an external remote controller RC 16, a clinician's programmer (CP) 18, an external trial modulator (ETM) 20, and an external charger 22.

The IPG 14 is physically connected via one or more percutaneous lead extensions 24 to the neuromodulation leads 12, which carry a plurality of electrodes 26 arranged in an array. In the illustrated embodiment, the neuromodulation leads 12 are percutaneous leads, and to this end, the electrodes 26 are arranged in-line along the neuromodulation leads 12. The number of neuromodulation leads 12 illustrated is two, although any suitable number of neuromodulation leads 12 can be provided, including only one. Alternatively, a surgical paddle lead in can be used in place of one or more of the percutaneous leads. As will be described in further detail below, the IPG 14 includes pulse generation circuitry that delivers electrical modulation energy in the form of a pulsed electrical waveform (i.e., a temporal series of electrical pulses) to the electrode array 26 in accordance with a set of modulation parameters.

The ETM 20 may also be physically connected via the percutaneous lead extensions 28 and external cable 30 to the neuromodulation leads 12. The ETM 20, which has similar pulse generation circuitry as the IPG 14, also delivers electrical modulation energy in the form of a pulse electrical waveform to the electrode array 26 accordance with a set of modulation parameters. The major difference between the ETM 20 and the IPG 14 is that the ETM 20 is a non-implantable device that is used on a trial basis after the neuromodulation leads 12 have been implanted and prior to implantation of the IPG 14, to test the responsiveness of the modulation energy delivered to the patient. Thus, any functions described herein with respect to the IPG 14 can likewise be performed with respect to the ETM 20.

The RC 16 may be used to telemetrically control the ETM 20 via a bi-directional RF communications link 32. Once the IPG 14 and neuromodulation leads 12 are implanted, the RC 16 may be used to telemetrically control the IPG 14 via a bi-directional RF communications link 34. Such control allows the IPG 14 to be turned on or off and to be programmed with different modulation parameter sets. The IPG 14 may also be operated to modify the programmed modulation parameters to actively control the characteristics of the electrical modulation energy output by the IPG 14. The CP 18 provides clinician detailed modulation parameters for programming the IPG 14 and ETM 20 in the operating room and in follow-up sessions.

The CP 18 may perform this function by indirectly communicating with the IPG 14 or ETM 20, through the RC 16, via an IR communications link 36. Alternatively, the CP 18 may directly communicate with the IPG 14 or ETM 20 via an RF communications link (not shown). The clinician detailed modulation parameters provided by the CP 18 are also used to program the RC 16, so that the modulation parameters can be subsequently modified by operation of the RC 16 in a stand-alone mode (i.e., without the assistance of the CP 18).

The external charger 22 is a portable device used to transcutaneously charge the IPG 14 via an inductive link 38. Once the IPG 14 has been programmed, and its power source has been charged by the external charger 22 or otherwise replenished, the IPG 14 may function as programmed without the RC 16 or CP 18 being present.

For purposes of brevity, the details of the CP 18, ETM 20, and external charger 22 will not be described herein. Details of exemplary embodiments of these devices are disclosed in U.S. Pat. No. 6,895,280, which is expressly incorporated herein by reference.

Figure 2:
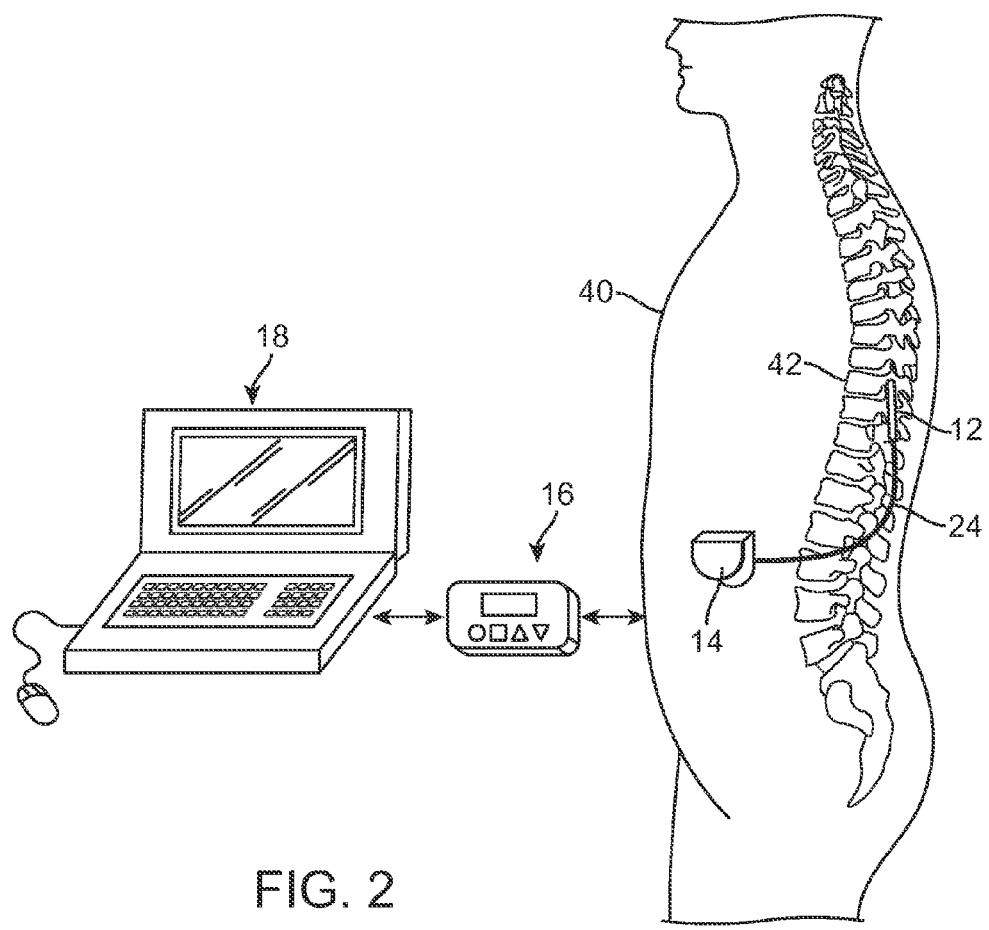
FIG. 2 is a plan view of the SCM system of FIG. 1 in use with a patient.
Figure 3:
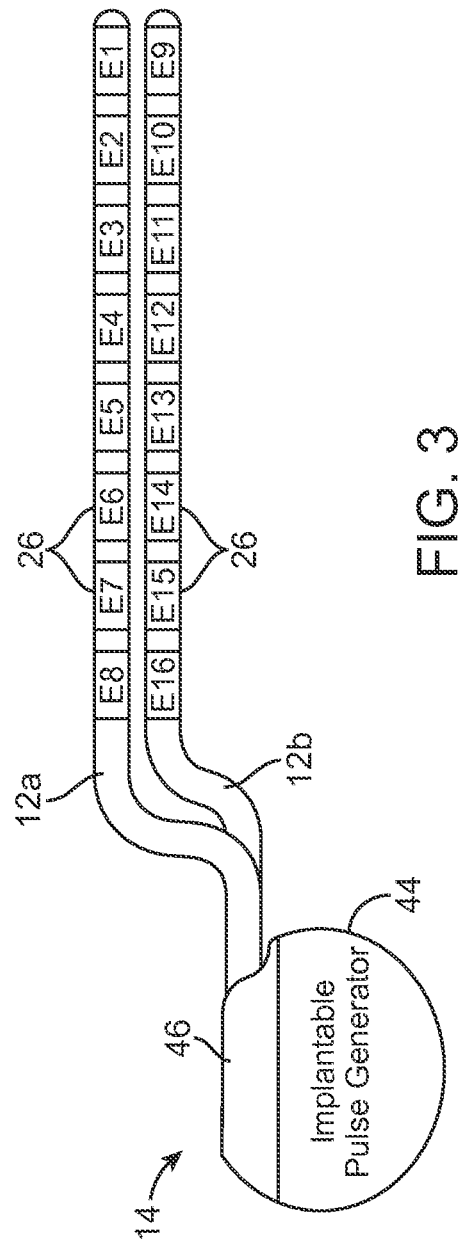
FIG. 3 is a profile view of an implantable pulse generator (IPG) and percutaneous leads used in the SCM system of FIG. 1.

As shown in FIG. 2, the neuromodulation leads 12 are implanted within the spinal column 42 of a patient 40. The preferred placement of the neuromodulation leads 12 is adjacent, i.e., resting upon, the spinal cord area to be stimulated. Due to the lack of space near the location where the neuromodulation leads 12 exit the spinal column 42, the IPG 14 is generally implanted in a surgically-made pocket either in the abdomen or above the buttocks. The IPG 14 may, of course, also be implanted in other locations of the patient's body. The lead extension 24 facilitates locating the IPG 14 away from the exit point of the neuromodulation leads 12. As there shown, the CP 18 communicates with the IPG 14 via the RC 16.

Referring now to Hg. 3, the external features of the neuromodulation leads 12 and the IPG 14 will be briefly described. One of the neuromodulation leads 12a has eight electrodes 26 (labeled E1-E8), and the other neuromodulation lead 12b has eight electrodes 26 (labeled E9-E16). The actual number and shape of leads and electrodes will, of course, vary according to the intended application. The IPG 14 comprises an outer case 44 for housing the electronic and other components (described in further detail below), and a connector 46 to which the proximal ends of the neuromodulation leads 12 mates in a manner that electrically couples the electrodes 26 to the electronics within the outer case 44. The outer case 44 is composed of an electrically conductive, biocompatible material, such as titanium, and forms a hermetically sealed compartment wherein the internal electronics are protected from the body tissue and fluids. In some cases, the outer case 44 may serve as an electrode.

As will be described in further detail below, the IPG 14 includes a battery and pulse generation circuitry that delivers the electrical modulation energy in the form of one or more electrical pulse trains to the electrode array 26 in accordance with a set of modulation parameters programmed into the IPG 14. Such modulation parameters may comprise electrode combinations, which define the electrodes that are activated as anodes (positive), cathodes (negative), and turned off (zero), percentage of modulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse duration (measured in microseconds), pulse rate (measured in pulses per second), and burst rate (measured as the modulation on duration X and modulation off duration Y).

Figure 4:
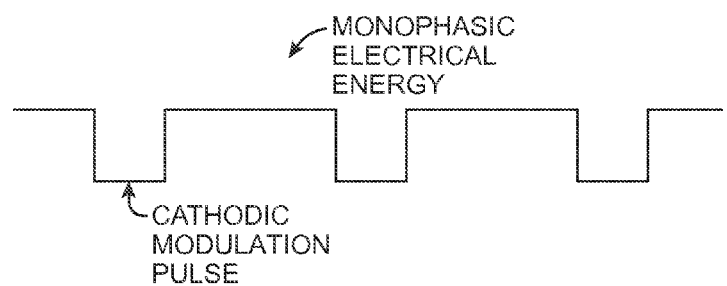
FIG. 4 is a plot of monophasic cathodic electrical modulation energy.

Electrical modulation will occur between two (or more) activated electrodes, one of which may be the IPG case 44. Modulation energy may be transmitted to the tissue in a monopolar or multipolar (e.g., bipolar, tripolar, etc.) fashion. Monopolar modulation occurs when a selected one of the lead electrodes 26 is activated along with the case of the IPG 14, so that modulation energy is transmitted between the selected electrode 26 and case. Bipolar modulation occurs when two of the lead electrodes 26 are activated as anode and cathode, so that modulation energy is transmitted between the selected electrodes 26. For example, electrode E3 on the first lead 12a may be activated as an anode at the same time that electrode E11 on the second lead 12a is activated as a cathode. Tripolar modulation occurs when three of the lead electrodes 26 are activated, two as anodes and the remaining one as a cathode, or two as cathodes and the remaining one as an anode. For example, electrodes E4 and E5 on the first lead 12a may be activated as anodes at the same time that electrode E12 on the second lead 12b is activated as a cathode The modulation energy may be delivered between a specified group of electrodes as monophasic electrical energy or multiphasic electrical energy. As illustrated in FIG. 4, monophasic electrical energy takes the form of an electrical pulse train that includes either all negative pulses (cathodic), or alternatively all positive pulses (anodic).

Figure 5A:
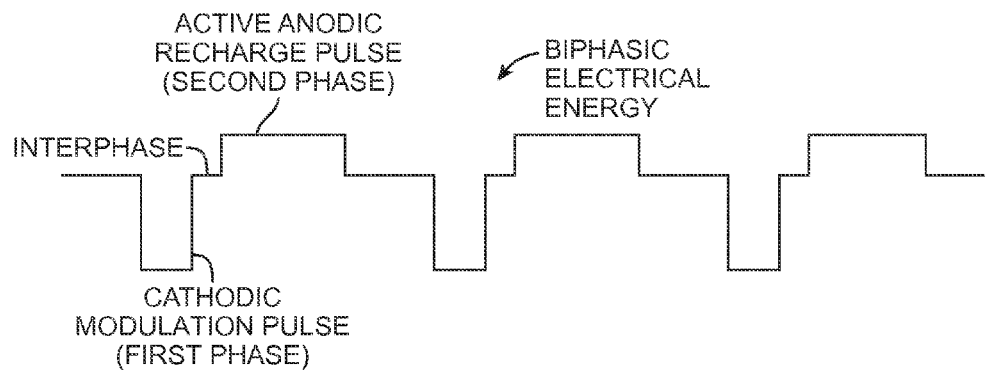
FIG. 5*a* is a plot of biphasic electrical modulation energy having a cathodic modulation pulse and an active charge recovery pulse.
Figure 5B:
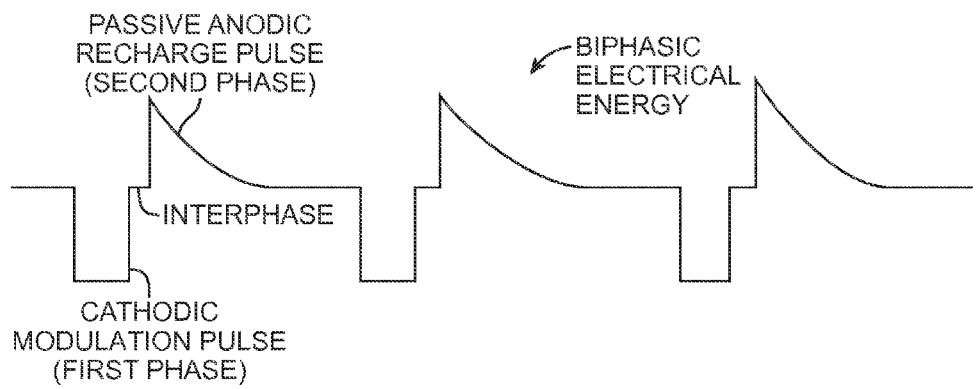
FIG. 5*b* is a plot of biphasic electrical modulation energy having a cathodic modulation pulse and a passive charge recovery pulse.

Multiphasic electrical energy includes a series of pulses that alternate between positive and negative. For example, as illustrated in FIGS. 5a and 5b, multiphasic electrical energy may include a series of biphasic pulses, with each biphasic pulse including a cathodic (negative) modulation pulse (during a first phase) and an anodic (positive) charge recovery pulse (during a second phase) that is generated after the modulation pulse to prevent direct current charge transfer through the tissue, thereby avoiding electrode degradation and cell trauma. That is, charge is conveyed through the electrode-tissue interface via current at an electrode during a modulation period (the length of the modulation pulse), and then pulled back off the electrode-tissue interface via an oppositely polarized current at the same electrode during a recharge period (the length of the charge recovery pulse).

The second phase may have an active charge recovery pulse (FIG. 5a), wherein electrical current is actively conveyed through the electrode via current or voltage sources, or the second phase may have a passive charge recovery pulse (FIG. 5b), wherein electrical current is passively conveyed through the electrode via redistribution of the charge flowing from coupling capacitances present in the circuit. Using active recharge, as opposed to passive recharge, allows faster recharge, while avoiding the charge imbalance that could otherwise occur. Another electrical pulse parameter in the form of an interphase can define the time period between the pulses of the biphasic pulse (measured in microseconds).

More significant to the present inventions, the SCM system 10 is configured for alternately delivering a sub-threshold electrical pulse train and a super-threshold pulse train to the spinal cord tissue of the patient, and specifically, alternately cycling the sub-threshold electrical pulse train on during high-energy consumption therapy periods and off during low-energy consumption therapy periods, as illustrated in FIG. 6. Thus, during the high energy consumption therapy periods when the sub-threshold electrical pulse train is cycled on, the patient is actively provided with therapy in the form of pain relief. In order to supplement the sub-threshold when the sub-threshold electrical pulse train is cycled off, the SCM system 10 is capable of delivering a super-threshold electrical pulse train to the spinal cord tissue of the patient, and specifically, alternately cycling the super-threshold electrical pulse train on during the low energy consumption therapy periods and off during the high energy consumption therapy periods, as illustrated in FIG. 6. The SCM system 10 alternately cycles the sub-threshold electrical pulse train and super-threshold electrical pulse train on and off in an automated manner (i.e., without user intervention once the cycling function is initiated).

As shown in FIG. 6, the high-energy consumption therapy periods are interleaved with the low-energy consumption therapy periods. Although the present inventions should not be so limited in their broadest aspects, the high-energy consumption therapy periods and the low-energy consumption therapy periods do no overlap each other, such that when one therapy period terminates, the next therapy period is initiated. Alternatively, a high-energy consumption therapy period and a low-energy consumption therapy period may slightly overlap with each other, and therefore, blend in with each other. The significance is that there will be a time period when only the sub-threshold electrical pulse train is delivered to the spinal cord tissue, and a time period when only the super-threshold electrical pulse train is delivered to the spinal cord tissue. The sub-threshold electrical pulse train and the super-threshold electrical pulse train may be delivered to the same spinal cord tissue region or different spinal cord tissue regions. The significance is that delivery of the super-threshold electrical pulse train provides pain relief to the patient that may not otherwise be provided when the sub-threshold electrical pulse train has been cycled off.

The sub-threshold electrical pulse train is delivered to the spinal cord tissue of the patient in accordance with a set of modulation parameters that are designed to provide sub-threshold therapy to the patient. Likewise, the super-threshold electrical pulse train is delivered to the spinal cord tissue of the patient in accordance with a set of modulation parameters that are designed to provide super-threshold therapy to the patient. Some embodiments deliver a sub-threshold pulse train using a pulse rate greater than 1500 Hz, and some embodiments deliver a sub-threshold pulse train using a pulse rate greater than 2500 Hz. Some embodiments deliver a sub-threshold pulse train using a pulse width less than 500 µs, some embodiments deliver a sub-threshold pulse train using a pulse width less than 100 µs, and deliver a sub-threshold pulse train using a pulse width less than 500 µs. For example, as shown in FIG. 7, an exemplary sub-threshold pulse train may be delivered at a relatively low pulse amplitude (e.g., 2.5 ma), a relatively high pulse rate (e.g., greater than 1500 Hz, preferably greater than 2500 Hz), and a relatively low pulse width (e.g., less than 500 µs, or less than 100 µs, or less than 50 µs), and an exemplary super-threshold pulse train may be delivered at a relatively high pulse amplitude (e.g., 5 ma), a relatively low pulse rate (e.g., less than 1500 Hz, preferably less than 500 Hz), and a relatively high pulse width (e.g., greater than 100 µs, or greater than 200 µs, or greater than 500 µs). Although both the sub-threshold electrical pulse train and the super-threshold electrical pulse train are illustrated as a biphasic pulse train having an active charge recovery phase, it should be appreciated that they can be biphasic cathodic or anodic pulse trains having a passive charge recovery phase.

In the preferred embodiment, the sub-threshold electrical pulse train and super-threshold electrical pulse train are cycled on and off in accordance with a predetermined tissue modulation regimen stored in the SCM system 10. The predetermined tissue modulation regimen may define a sub-threshold modulation program and a super-threshold modulation program, in which case, the sub-threshold electrical pulse train may be delivered to the spinal cord tissue in accordance with the sub-threshold modulation program, and the super-threshold electrical pulse train may be delivered to the spinal cord tissue in accordance with the super-threshold modulation program.

The SCM system 10 may modify one or both of the sub-threshold electrical pulse train and the super-threshold electrical pulse train (e.g., by modifying one of the modulation programs or otherwise the modulation parameters) in response to receiving input from the user. In an optional embodiment, the SCM system 10 may derive a set of super-threshold modulation parameters from a set of sub-threshold modulation parameters, or vice versa, using one of the techniques described in U.S. Provisional Patent Application Ser. No. 61/801,917, entitled "Systems and Methods for Delivering Sub-threshold Therapy to a Patient," which is expressly incorporated herein by reference.

In one embodiment, the SCM system 10 stores a time schedule in response to receiving input from the user, and defines the high-energy consumption therapy periods and low-energy consumption therapy periods in accordance with the time schedule. The time schedule may define absolute times for the high-energy consumption therapy periods and low-energy consumption therapy periods (e.g., initiate high-energy consumption therapy period at 9:00 am; terminate the high-energy consumption therapy period and initiate the low-energy consumption therapy period at 11:00 am; terminate the low-energy consumption therapy period and initiate the high-energy consumption therapy period at 2:00 pm, etc.) or the time schedule may define relative times for the high-energy consumption therapy periods and low-energy consumption therapy periods (e.g., terminate high-energy consumption therapy period and initiate the low-energy consumption therapy period two hours after the high-energy consumption therapy period has been initiated; terminate the low-energy consumption therapy period and initiate the high-energy consumption therapy period three hours after the high-energy consumption therapy has been terminated, etc.).

In an optional embodiment, the SCM system 10 detects a patient activity level (expenditure of energy), and defines the high-energy consumption therapy periods during times when the patient activity level is relatively high, and defines the low-energy consumption therapy periods during times when the patient activity level is relatively low. In one technique, the physical activity level of the patient is estimated from the magnitude of time varying electrical parameter data measured from the electrodes 26 or data measured from other sensors (impedance, activity, accelerometer, etc.), as described in U.S. Parent application Ser. No. 12/024,947, entitled "Neurostimulation System and Method for Measuring Patient Activity," which is expressly incorporated herein by reference. In another technique, the physical activity level of the patient is estimated from a frequency that an orientation sensitive component implanted within the patient detects a change in orientation, as described in U.S. patent application Ser. No. 13/446,191, entitled "Sensing Device for Indicating Posture of Patient Implanted with a Neurostimulation Device, which is expressly incorporated herein by reference.

Figure 8:
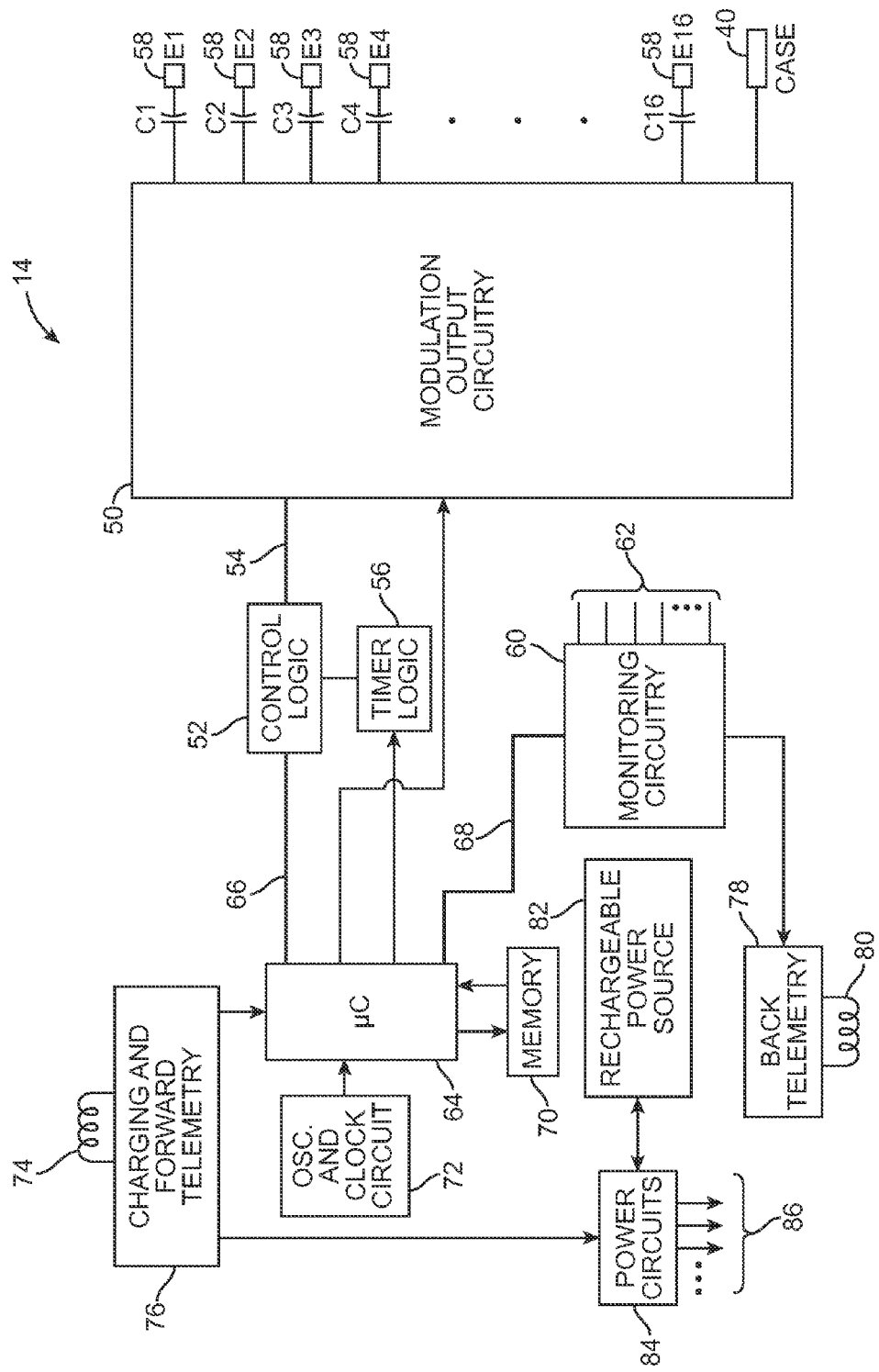
FIG. 8 is a block diagram of the internal components of the IPG of FIG. 3.

Turning next to FIG. 8, the main internal components of the IPG 14 will now be described. The IPG 14 includes modulation output circuitry 50 configured for generating electrical modulation energy in accordance with a defined pulsed waveform having a specified pulse amplitude, pulse rate, pulse width, pulse shape, and burst rate under control of control logic 52 over data bus 54. Control of the pulse rate and pulse width of the electrical waveform is facilitated by tinier logic circuitry 56, which may have a suitable resolution, e.g., 10 µs. The modulation energy generated by the modulation output circuitry 50 is output via capacitors C1-C16 to electrical terminals 58 corresponding to the electrodes 26. The analog output circuitry 50 may either comprise independently controlled current sources for providing modulation pulses of a specified and known amperage to or from the electrodes 26, or independently controlled voltage sources for providing modulation pulses of a specified and known voltage at the electrodes 26.

Any of the N electrodes may be assigned to up to k possible groups or timing "channels." In one embodiment, k may equal four. The timing channel identifies which electrodes are selected to synchronously source or sink current to create an electric field in the tissue to be stimulated. Thus, multiple timing channels can be utilized to concurrently deliver electrical current (by interlacing the pulses of electrical pulse trains together) to multiple tissue regions of the patient. Amplitudes and polarities of electrodes on a channel may vary, e.g., as controlled by the RC 16. External programming software in the CP 18 is typically used to set modulation parameters including amplitude, pulse rate and pulse duration for the electrodes of a given channel, among other possible programmable features.

The N programmable electrodes can be programmed to have a positive (sourcing current), negative (sinking current), or off (no current) polarity in any of the k channels. Moreover, each of the N electrodes can operate in a multipolar (e.g., bipolar) mode, e.g., where two or more electrode contacts are grouped to source/sink current at the same time. Alternatively, each of the N electrodes can operate in a monopolar mode where, e.g., the electrodes associated with a channel are configured as cathodes (negative), and the case electrode (i.e., the IPG case) is configured as an anode (positive).

Further, the amplitude of the current pulse being sourced or sunk to or from a given electrode may be programmed to one of several discrete current levels, e.g., between 0 to 10 mA in steps of 0.1 mA. Also, the pulse duration of the current pulses is preferably adjustable in convenient increments, e.g., from 0 to 1 milliseconds (ms) in increments of 10 microseconds (µs). Similarly, the pulse rate is preferably adjustable within acceptable limits, e.g., from 0 to 50K pulses per second (pps). Other programmable features can include slow start/end ramping, burst modulation cycling (on for X time, off for Y time), interphase, and open or dosed loop sensing modes.

The operation of this modulation output circuitry 50, including alternative embodiments of suitable output circuitry for performing the same function of generating modulation pulses of a prescribed amplitude and duration, is described more fully in U.S. Pat. Nos. 6,516,227 and 6,993,384, which are expressly incorporated herein by reference.

The IPG 14 further comprises monitoring circuitry 60 configured for monitoring the status of various nodes or other points 62 throughout the IPG 14, e.g., power supply voltages, temperature, battery voltage, and the like. The monitoring circuitry 60 may also be configured for measuring electrical parameter data from the electrodes 26 or other information from other sensors needed to determine the current activity level of the patient. The IPG 14 further comprises processing circuitry in the form of a microcontroller (µC) 64 that controls the control logic over data bus 66, and obtains status data from the monitoring circuitry 60 via data bus 68. The IPG 14 additionally controls the timer logic 58. The IPG 14 further comprises memory 70 and oscillator and dock circuitry 72 coupled to the microcontroller 64. The microcontroller 64, in combination with the memory 70 and oscillator and dock circuitry 72, thus comprise a microprocessor system that carries out a program function in accordance with a suitable program stored in the memory 70. Alternatively, for some applications, the function provided by the microprocessor system may be carried out by a suitable state machine.

Thus, the microcontroller 64 generates the necessary control and status signals, which allow the microcontroller 64 to control the operation of the IPG 14 in accordance with a selected operating program and modulation program stored in the memory 70. In controlling the operation of the IPG 14, the microcontroller 64 is able to individually generate an electrical pulse train at the electrodes 26 using the modulation output circuitry 50, in combination with the control logic 52 and timer logic 56, thereby allowing each electrode 26 to be paired or grouped with other electrodes 26, including the monopolar case electrode. In accordance with modulation parameters stored within the memory 70, the microcontroller 64 may control the polarity, amplitude, rate, pulse duration and timing channel through which the modulation pulses are provided.

Thus, it can be appreciated that, under control of the microcontroller 64, the modulation output circuitry 50 is configured for outputting a k number of individual electrical pulse trains respectively in a k number of timing channels to the electrical terminals 56, with each electrical pulse train including biphasic pulses as shown in FIGS. 5a and 5b. In the IPG 14, up to four stimulation programs may be stored in the memory 70, with each stimulation program having four timing channels. Thus, each modulation program defines four sets of modulation parameters for four respective timing channels. Of course, the IPG 14 may have less or more than four modulation programs, and less or more than four timing channels for each modulation program. The memory 70 also stores a time schedule, which as discussed above, defines the beginning and end of each of the high-energy consumption periods and low-energy consumption periods. The memory 70 may optionally store any threshold values to which the electrical parameter measurements or other measurements are compared to facilitate determining whether patient activity is relatively high or relatively low.

Significantly, at least one of these modulation programs will be a sub-threshold modulation program designed to treat chronic pain in a region of the patient (e.g., the lower back) and at least one of these modulation programs will be a super-threshold program designed to treat the chronic pain in the same region of the patient. The sub-threshold and super-threshold modulation programs, along with the time schedule, may be stored as a hybrid modulation program, or the sub-threshold and super-threshold modulation programs may be stored separately and accessed in accordance with the time schedule.

The microcontroller 64 accesses the sub-threshold modulation program and super-threshold modulation program from memory 70, and controls the modulation output circuitry 50 in a manner that cycles the sub-threshold electrical pulse train on during the high-energy consumption time periods and off during the low-energy consumption time periods, and cycles the super-threshold electrical pulse train on during the low-energy consumption time periods and off during the high-energy consumption time periods. The microcontroller 64 can perform this cycling function based on the time schedule stored in the memory 70 or a determined patient activity level.

Although the sub-threshold electrical pulse train and super-threshold electrical pulse train are illustrated in FIGS. 6 and 7 as being cycled on and off in a single timing channel, it should be appreciated that multiple sub-threshold electrical pulse trains and multiple super-threshold electrical pulse trains can be cycled on and off respectively during multiple timing channels.

Alternatively, in the same manner described in U.S. Provisional Patent Application Ser. No. 61/801,917, entitled "Systems and Methods for Delivering Sub-threshold Therapy to a Patient," which is expressly incorporated herein by reference, only the sub-threshold modulation program is stored in memory 70, in which case, the microcontroller 64 may derive the super-threshold modulation program from the stored sub-threshold modulation program, or only the super-threshold modulation program is stored in memory 70, in which case, the microcontroller 64 may derive the sub-threshold modulation program from the stored super-threshold modulation program The IPG 14 further comprises an alternating current (AC) receiving coil 74 for receiving programming data (e.g., the operating program, modulation programs including the parameters, and/or a time schedule) from the RC 16 (shown in FIG. 1) in an appropriate modulated carrier signal, and charging and forward telemetry circuitry 76 for demodulating the carrier signal it receives through the AC receiving coil 74 to recover the programming data, which programming data is then stored within the memory 70, or within other memory elements (not shown) distributed throughout the IPG 14.

The IPG 14 further comprises back telemetry circuitry 78 and an alternating current (AC) transmission coil 80 for sending informational data sensed through the monitoring circuitry 60 to the RC 16. The back telemetry features of the IPG 14 also allow its status to be checked. For example, when the RC 16 initiates a programming session with the IPG 14, the capacity of the battery is telemetered, so that the external programmer can calculate the estimated time to recharge. Any changes made to the current stimulus parameters are confirmed through back telemetry, thereby assuring that such changes have been correctly received and implemented within the implant system. Moreover, upon interrogation by the RC 16, all programmable settings stored within the IPG 14 may be uploaded to the RC 16. Significantly, the back telemetry features allow raw or processed electrical parameter data (or other parameter data) previously stored in the memory 70 to be downloaded from the IPG 14 to the RC 16, which information can be used to track the physical activity of the patient.

The IPG 14 further comprises a rechargeable power source 82 and power circuitry 84 for providing the operating power to the IPG 14. The rechargeable power source 82 may, e.g., comprise a lithium-ion or lithium-ion polymer battery. The rechargeable battery 82 provides an unregulated voltage to the power circuitry 84. The power circuitry 84, in turn, generate the various voltages 86, some of which are regulated and some of which are not, as needed by the various circuits located within the IPG 14. The rechargeable power source 82 is recharged using rectified AC power (or DC power converted from AC power through other means, e.g., efficient AC-to-DC converter circuits, also known as "inverter circuits") received by the AC receiving coil 134. To recharge the power source 82, an external charger (not shown), which generates the AC magnetic field, is placed against, or otherwise adjacent, to the patient's skin over the implanted IPG 14. The AC magnetic field emitted by the external charger induces AC currents in the AC receiving coil 74. The charging and forward telemetry circuitry 76 rectifies the AC current to produce DC current, which is used to charge the power source 82. While the AC receiving coil 74 is described as being used for both wirelessly receiving communications (e.g., programming and control data) and charging energy from the external device, it should be appreciated that the AC receiving coil 74 can be arranged as a dedicated charging coil, while another coil, such as coil 80, can be used for bi-directional telemetry.

It should be noted that the diagram of FIG. 8 is functional only, and is not intended to be limiting. Those of skill in the art, given the descriptions presented herein, should be able to readily fashion numerous types of IPG circuits, or equivalent circuits, that carry out the functions indicated and described, which functions include not only producing a stimulus current or voltage on selected groups of electrodes, but also the ability to measure electrical parameter data at an activated or non-activated electrode.

Additional details concerning the above-described and other IPGs may be found in U.S. Pat. No. 6,516,227, U.S. Patent Publication No. 2003/0139781, and U.S. patent application Ser. No. 11/138,632, entitled "Low Power Loss Current Digital-to-Analog Converter Used in an Implantable Pulse Generator," which are expressly incorporated herein by reference. It should be noted that rather than an IPG, the SCM system 10 may alternatively utilize an implantable receiver-modulator (not shown) connected to the modulation leads 12. In this case, the power source, e.g., a battery, for powering the implanted receiver, as well as control circuitry to command the receiver-modulator, will be contained in an external controller inductively coupled to the receiver-modulator via an electromagnetic link. Data/power signals are transcutaneously coupled from a cable-connected transmission coil placed over the implanted receiver-modulator. The implanted receiver-modulator receives the signal and generates the modulation in accordance with the control signals.

Figure 9:
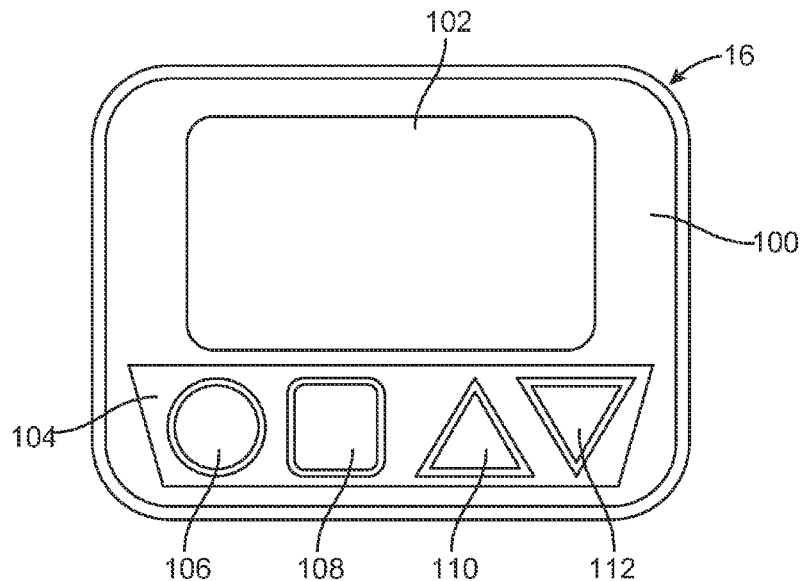
FIG. 9 is front view of a remote control (RC) used in the SCM system of FIG. 1.

Referring now to FIG. 9, one exemplary embodiment of an RC 16 will now be described. As previously discussed, the RC 16 is capable of communicating with the IPG 14, CP 18, or ETS 20. The RC 16 comprises a casing 100, which houses internal componentry (including a printed circuit board (PCB)), and a lighted display screen 102 and button pad 104 carried by the exterior of the casing 100. In the illustrated embodiment, the display screen 102 is a lighted flat panel display screen, and the button pad 104 comprises a membrane switch with metal domes positioned over a flex circuit, and a keypad connector connected directly to a printed circuit board (PCB). In an optional embodiment, the display screen 102 has touchscreen capabilities. The button pad 104 includes a multitude of buttons 106, 108, 110, and 112, which allow the IPG 14 to be turned ON and OFF, provide for the adjustment or setting of modulation parameters within the IPG 14, and provide for selection between screens.

In the illustrated embodiment, the button 106 serves as an ON/OFF button that can be actuated to turn the IPG 14 ON and OFF. The button 108 serves as a select button that can be actuated to switch the RC 16 between screen displays and/or parameters. The buttons 100 and 112 serve as up/down buttons that can be actuated to increment or decrement any of modulation parameters of the pulsed electrical train generated by the IPG 14, including pulse amplitude, pulse width, and pulse rate. For example, the selection button 108 can be actuated to place the RC 16 in a "Pulse Amplitude Adjustment Mode," during which the pulse amplitude can be adjusted via the up/down buttons 110, 112, a "Pulse Width Adjustment Mode," during which the pulse width can be adjusted via the up/down buttons 110, 112, and a "Pulse Rate Adjustment Mode," during which the pulse rate can be adjusted via the up/down buttons 110, 112. Alternatively, dedicated up/down buttons can be provided for each modulation parameter. Rather than using up/down buttons, any other type of actuator, such as a dial, slider bar, or keypad, can be used to increment or decrement the modulation parameters. The selection button 108 can also be actuated to place the RC 16 in a "Scheduling Mode," during which the beginning and ending of each of the high-energy consumption periods and low-energy consumption periods can be defined or adjusted.

Figure 10:
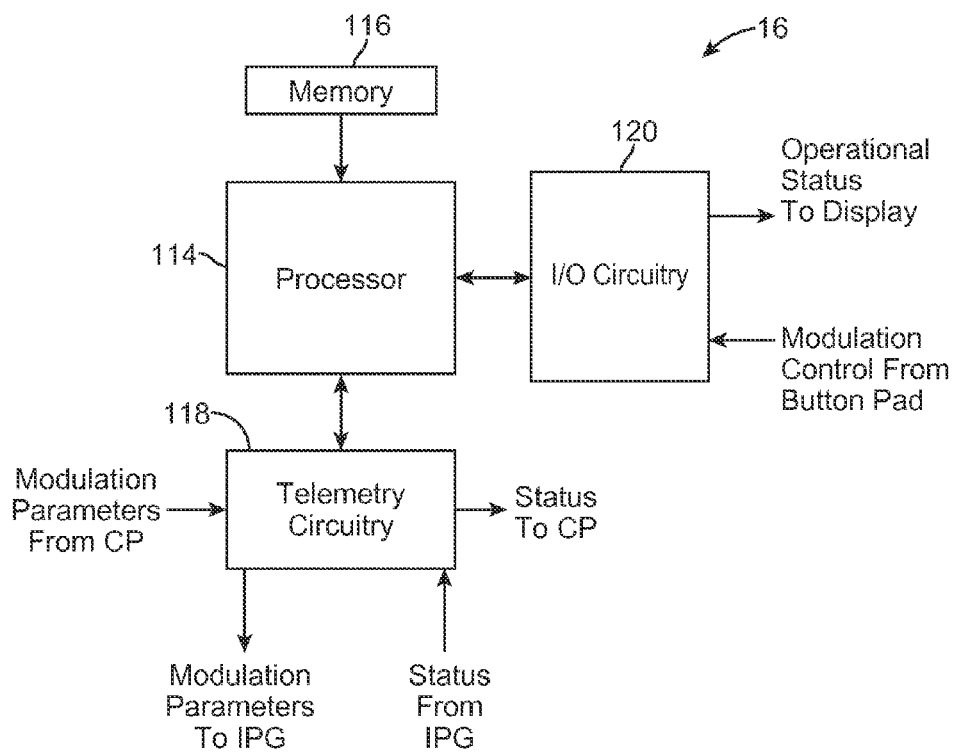
FIG. 10 is a block diagram of the internal components of the RC of FIG. 9.

Referring to FIG. 10, the internal components of an exemplary RC 16 will now be described. The RC 16 generally includes a controller/processor 114 (e.g., a microcontroller), memory 116 that stores an operating program for execution by the controller/processor 114, as well as modulation programs defining modulation parameter sets; input/output circuitry, and in particular, telemetry circuitry 118 for outputting modulation programs and scheduling information to the IPG 14 or otherwise directing the IPG 14 to deliver modulation energy in accordance with the modulation parameters and scheduling information, and receiving status information from the IPG 14; and input/output circuitry 120 for receiving modulation control signals from the button pad 104 or other control elements and transmitting status information to the display screen 102 (shown in FIG. 9).

Although, in the illustrated embodiment, the scheduling information is described as being transmitted from the RC 16 to the IPG 14, it should be appreciated that the RC 16 may simply transmit control signals to the IPG 14 to cycle the super-threshold and sub-threshold therapies on and off in accordance with the time schedule stored in the memory 66. Further details of the functionality and internal componentry of the RC 16 are disclosed in U.S. Pat. No. 6,895,280, which has previously been incorporated herein by reference.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A neuromodulation system, comprising:
    modulation output circuitry configured to deliver therapeutic electrical energy including therapeutic sub-threshold electrical energy and therapeutic a super-threshold electrical energy, wherein the modulation output circuitry is configured to deliver the sub-threshold electrical energy below a patient-perception threshold and is configured to deliver the super-threshold electrical energy above the patient-perception threshold, the patient-perception threshold being a boundary below which a patient does not sense delivery of the electrical energy and above which the patient does sense delivery of the electrical energy; and
    control circuitry configured to control the modulation output circuitry to deliver the therapeutic electrical energy using alternating cycles of high-energy consumption time periods during which the patient does not sense delivery of the electrical energy and low-energy consumption time periods during which the patient does sense delivery of the electrical energy, wherein the control circuitry is configured to control the modulation circuitry to deliver the sub-threshold electrical energy below the patient-perception threshold during the high-energy consumption periods and deliver the super-threshold electrical energy above the patient-perception threshold during the low-energy consumption periods.

2. The neuromodulation system of claim 1, wherein:
    the neuromodulation system includes a spinal cord modulation (SCM) system;
    the patient-perception threshold being a boundary below which the patient does not experience paresthesia and above which the patient does experience paresthesia; and the modulation system is configured to deliver therapeutic electrical energy effective to alleviate pain, including sub-threshold electrical energy effective to alleviate pain without paresthesia and super-threshold electrical energy effective to alleviate pain with paresthesia.

3. The neuromodulation system of claim 1, further comprising a plurality of electrical terminals configured to be respectively coupled to a plurality of electrodes, the modulation output circuitry being operably connected to the plurality of electrical terminals to deliver the therapeutic electrical energy to specified groups of electrodes.

4. The neuromodulation system of claim 3, wherein the modulation system is configured to use a specified group of electrodes to deliver both the sub-threshold electrical energy and the super-threshold electrical energy.

5. The neuromodulation system of claim 3, wherein the modulation system is configured to use a specified group of electrodes to deliver the sub-threshold electrical energy and use another group of electrodes to deliver the super-threshold electrical energy.

6. The neuromodulation system of claim 3, further comprising independently-controlled current sources or independently controlled voltage sources, wherein the modulation system is configured to control a percentage of electrical energy assigned to each electrode.

7. The neuromodulation system of claim 1, wherein the therapeutic sub-threshold electrical energy includes a pulse train with a pulse rate greater than 1500 Hz, and the therapeutic super-threshold electrical energy includes a pulse train with a pulse rate less than 1500 Hz.

8. The neuromodulation system of claim 1, wherein the therapeutic sub-threshold electrical energy includes a pulse train with a pulse duration less than 500 µs, and the therapeutic super-threshold electrical energy includes a pulse train with a pulse duration greater than 500 µs.

9. The neuromodulation system of claim 1, further comprising a user interface configured to receive a user input, wherein the control circuitry is configured to modify at least one of the sub-threshold electrical energy and the super-threshold electrical pulse energy in response to the user input.

10. The neuromodulation system of claim 1, further comprising a memory to store a time schedule defining hours for operating in the high-energy consumption time periods and hours for operating in the low-energy consumption time periods, and a user interface configured to receive a user input, wherein the control circuitry is configured to store the time schedule in response to the user input, and to use the stored time schedule to control timing for cycling the sub-threshold electrical energy below the patient-perception threshold and the super-threshold electrical energy above the patient-perception threshold.

11. The neuromodulation system of claim 10, wherein the time schedule defines absolute times.

12. The neuromodulation system of claim 10, wherein the time schedule defines relative times.

13. The neuromodulation system of claim 1, further comprising a sensor configured to detect a patient activity level, wherein the control circuitry is configured to use the sensor to determine times of low patient activity to identify the high-energy consumption time periods and times of high patient activity to identify the low-energy consumption time periods, and to deliver the sub-threshold electrical energy during the times of low patient activity and deliver the super-threshold electrical energy during the times of low patient activity.

14. The neuromodulation system of claim 1, further comprising memory configured to store a programmed tissue modulation regimen, wherein the control circuitry is configured to use the programmed tissue modulation regimen to control the modulation output circuitry to automatically cycle each of the sub-threshold electrical energy and the super-threshold electrical energy on and off in accordance with the programmed tissue modulation regimen.

15. The neuromodulation system of claim 14, wherein the programmed tissue modulation regimen defines a sub-threshold modulation program and a super-threshold modulation program, and the modulation output circuitry is configured to deliver the sub-threshold electrical energy in accordance with the sub-threshold modulation program, and deliver the super-threshold electrical energy in accordance with the super-threshold modulation program.

16. The neuromodulation system of claim 1, wherein the system includes a spinal cord modulation (SCM) system, comprising:
   a plurality of electrical terminals configured to be respectively coupled to a plurality of electrodes;
   wherein the modulation output circuitry is operably connected to the plurality of electrical terminals to deliver therapeutic electrical energy for alleviating pain to specified groups of electrodes, the therapeutic electrical energy including the sub-threshold electrical energy and the super-threshold electrical energy; and
   the SCM system including a memory with a time schedule programmed in the memory, the control circuitry configured to use the time schedule to automatically cycle the sub-threshold electrical energy and the super-threshold electrical energy.

17. The SCM system of claim 16, wherein the therapeutic sub-threshold electrical energy includes a pulse train with a pulse rate greater than 1500 Hz, the therapeutic super-threshold electrical energy includes a pulse train with a pulse rate less than 1500 Hz.

18. The SCM system of claim 16, wherein the therapeutic sub-threshold electrical energy includes a pulse train with a pulse duration less than 500 µs, and the therapeutic super-threshold electrical energy includes a pulse train with a pulse duration greater than 500 µs.

19. The SCM system of claim 16, further comprising a sensor configured to detect a patient activity level, wherein the control circuitry is configured to use the sensor to determine times of low patient activity and times of high patient activity, and to deliver the sub-threshold electrical energy during the times of low patient activity and deliver the super-threshold electrical energy during the times of low patient activity.

20. The SCM system of claim 16, further comprising a user interface configured to receive a user input, wherein the control circuitry is configured to modify at least one of the sub-threshold electrical energy and the super-threshold electrical pulse energy in response to the user input.

* * * * *